United States Patent
Hashimoto et al.

(10) Patent No.: US 9,730,866 B2
(45) Date of Patent: Aug. 15, 2017

(54) EMULSION COMPOSITION

(71) Applicant: FUJIFILM CORPORATION, Minato-ku, Tokyo (JP)

(72) Inventors: Shinichi Hashimoto, Kanagawa (JP); Shigetomo Tsujihata, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 14/801,857

(22) Filed: Jul. 17, 2015

(65) Prior Publication Data

US 2015/0320652 A1 Nov. 12, 2015

Related U.S. Application Data

(63) Continuation of application No. PCT/JP2013/084537, filed on Dec. 24, 2013.

(30) Foreign Application Priority Data

Jan. 31, 2013 (JP) .................................. 2013-017644

(51) Int. Cl.
| | | |
|---|---|---|
| A61K 8/06 | (2006.01) | |
| A61K 31/506 | (2006.01) | |
| A61K 9/107 | (2006.01) | |
| A61Q 7/00 | (2006.01) | |
| A61K 8/34 | (2006.01) | |
| A61K 8/36 | (2006.01) | |
| A61K 8/49 | (2006.01) | |
| A61K 8/60 | (2006.01) | |
| A61K 8/92 | (2006.01) | |

(52) U.S. Cl.
CPC ................ *A61K 8/06* (2013.01); *A61K 8/062* (2013.01); *A61K 8/34* (2013.01); *A61K 8/345* (2013.01); *A61K 8/361* (2013.01); *A61K 8/4953* (2013.01); *A61K 8/60* (2013.01); *A61K 8/922* (2013.01); *A61K 9/107* (2013.01); *A61K 31/506* (2013.01); *A61Q 7/00* (2013.01); *A61K 2800/21* (2013.01); *A61K 2800/412* (2013.01)

(58) Field of Classification Search
CPC ...... A61K 8/44; A61K 8/4953; A61K 31/505; A61K 2300/00; A61K 31/506; A61K 47/183; A61K 8/27; A61K 8/345; A61K 9/0014; A61K 2800/70; A61K 2800/782; A61K 31/12; A61K 31/122; A61K 8/0295
See application file for complete search history.

(56) References Cited

U.S. PATENT DOCUMENTS

| | | |
|---|---|---|
| 5,547,661 A | 8/1996 | Sun et al. |
| 6,265,412 B1 | 7/2001 | Kimura et al. |
| 2003/0180278 A1 | 9/2003 | Hoppe et al. |
| 2004/0162301 A1 | 8/2004 | Imamura et al. |

FOREIGN PATENT DOCUMENTS

| | | |
|---|---|---|
| JP | H02-62818 A | 3/1990 |
| JP | 2003-12468 A | 1/2003 |
| JP | 2004-155689 A | 6/2004 |
| JP | 2004-155690 A | 6/2004 |
| JP | 2005-519887 A | 7/2005 |
| JP | 2010-180132 A | 8/2010 |
| JP | 2010-222283 A | 10/2010 |
| JP | 2011-51980 A | 3/2011 |
| JP | 2013-520400 A | 6/2013 |
| WO | 9961059 A1 | 12/1999 |
| WO | 02092092 A1 | 11/2002 |
| WO | 2007/023396 A2 | 3/2007 |
| WO | WO2009/158687 A1 * | 12/2009 ............... A61K 9/51 |

OTHER PUBLICATIONS

Toshio et al., JP2011-51980A, published Mar. 2011, translation enclosed.*
International Search Report issued in International Application No. PCT/JP2013/084537 on Jan. 28, 2014.
Written Opinion of the ISA issued in International Application No. PCT/JP2013/084537 on Jan. 28, 2014.
Chinnian D, Asker AF., Photostability profiles of minoxidil solutions., PDA J Pharm Sci Technol., 1996, 50(2), p. 94-98.
Contact Dermatitis 1994, 30, 1-6.
Contact Dermatitis 2005, 53, 247-259.
The Journal of Investigative Dermatology 1977, 69, 219-222.
Extended European Search Report dated Nov. 27, 2015 from the EPO in an European patent application corresponding to the instant patent application.
Office Action dated Feb. 9, 2016, issued by Japan Patent Office in a Japanese patent application corresponding to the instant patent application. A translation of the Japanese Office Action is submitted herewith.
Partial English language translation of the following: Office action dated Aug. 2, 2016 from the JPO in a Japanese patent application corresponding to the instant patent application.
Chinese Office Action dated Jun. 27, 2016 in corresponding Chinese Patent Application and a Partial English Translation thereof.
Communication dated Apr. 18, 2017 from the European Patent Office in counterpart Application No. 13873237.5.
Datebase WPI Week 200440 Thomson Scientific, London, GB; AN2004-424359 XP002745441.
Chinese Office Action dated May 5, 2017 in corresponding Chinese Patent Application No. 201380071435.9 and Partial English Translation thereof.

* cited by examiner

Primary Examiner — Audrea Buckley
(74) Attorney, Agent, or Firm — SOLARIS Intellectual Property Group, PLLC

(57) ABSTRACT

An emulsion composition includes a compound having a diaminopyrimidine skeleton, at least one fatty acid component selected from the group consisting of a fatty acid having a total carbon number of 14 or more and a salt thereof, and an aqueous medium in an amount of 50% by mass or more with respect to the mass of the emulsion composition. The total amount of monohydric alcohol having a total carbon number of 3 or less and dihydric alcohol having a total carbon number of 3 or less is less than 10% by mass with respect to the mass of the emulsion composition. The emulsion composition has a pH of 6.5 or more.

11 Claims, No Drawings

EMULSION COMPOSITION

CROSS-REFERENCE TO RELATED APPLICATIONS

This application is a continuation application of International Application No. PCT/JP2013/084537, filed Dec. 24, 2013, the disclosure of which is incorporated herein by reference in its entirety. Further, this application claims priority from Japanese Patent Application No. 2013-017644, filed Jan. 31, 2013, the disclosure of which is incorporated herein by reference in its entirety.

TECHNICAL FIELD

The present invention relates to an emulsion composition.

BACKGROUND ART

Examples of compounds having a diaminopyrimidine skeleton (hereinafter, referred to as "diaminopyrimidine derivatives") include minoxidil (2,4-diamino-6-piperidinopyrimidine-3-oxide), and compounds having a diaminopyrimidine skeleton are known as compounds having therapeutic and prophylactic activity on male hormonal alopecia. In Japanese Patent Application Laid-Open (JP-A) No. 2004-155689 and JP-A No. 2004-155690, there is a disclosure that diaminopyrimidine derivatives are dissolved in water solvents using 50% or more of ethanol because diaminopyrimidine derivatives have low solubility in water.

However, with respect to compositions containing ethanol at 50% or more, there is a concern about, for example, irritation to the scalp by ethanol, as is disclosed in *Contact Dermatitis* 1994, 30, 1-6 and *The Journal of Investigative Dermatology* 1977, 69, 219-222. In view of this, liquid compositions in which a specific solubilizer is contained for the purpose of solubilizing minoxidil and in which the content of ethanol is set to be less than 50% are known. As such a solubilizer, for example, bile acid or a salt thereof is proposed in JP-A No. 2010-180132, and a multimeric protein or the like is proposed in JP-A No. 2010-222283.

Moreover, various pharmaceutical preparations which exert an excellent hair-restoring or hair-growing effect through external application of minoxidil have been proposed.

For example, in JP-A No. 2011-051980, an emulsion or micelle preparation that contains a higher fatty acid, polyoxyethylene hydrogenated castor oil, a lower alcohol, and a polyhydric alcohol is proposed in order to enhance the delivery of minoxidil to the trichocyst. Here, with respect to the pharmaceutical preparation described in JP-A No. 2011-051980, it is described that lower alcohols are required for inclusion of minoxidil in a high concentration.

In JP-A No. 2005-519887, a preparation containing a lipophilic component and a hydrophilic component is proposed in which a higher fatty acid and a component such as triethanolamine, monopropylene glycol, glycerol, or polyvinylpyrrolidone are contained in order to enhance the penetration of minoxidil. In addition, in JP-A No. 2005-519887, a preparation in which propylene glycol is contained substantially in an amount of as much as 28% by weight is disclosed. Propylene glycol is known to cause strong skin irritation, as disclosed in *Contact Dermatitis* 2005, 53, 247-259.

SUMMARY OF INVENTION

Technical Problem

As described above, it is known that monohydric or dihydric alcohols having 3 or fewer carbon atoms cause strong skin irritation. We have found that, in a case in which an emulsion composition containing a diaminopyrimidine derivative but not containing a monohydric or dihydric alcohol having a total of 3 or fewer carbon atoms such as ethanol or propylene glycol is stored, decomposition of the diaminopyrimidine derivative may occur with a lapse of time, the stability of the emulsion also deteriorates with a lapse of time, and aggregation and coalescence of emulsified particles occur.

The present invention has been made in view of the above circumstances, and addresses provision of an emulsion composition containing a diaminopyrimidine derivative, and having favorable emulsion stability and favorable stability of the diaminopyrimidine derivative.

Solution to Problem

The inventors of the present invention conducted studies, aiming to solve the problem described above, as a result of which the inventors have found that, by using a fatty acid having a total carbon number of 14 or more or a salt thereof and setting the pH to 6.5 or more, favorable emulsion stability and favorable stability of the diaminopyrimidine derivative can be both achieved without substantially containing any monohydric or dihydric alcohols having a total carbon number of 3 or less, which would cause strong skin irritation.

Specifically, the present invention include the following.

[1] An emulsion composition, including:
a compound having a diaminopyrimidine skeleton;
at least one fatty acid component selected from the group consisting of a fatty acid having a total carbon number of 14 or more and a salt thereof; and
an aqueous medium in an amount of 50% by mass or more with respect to the mass of the emulsion composition,
the total amount of a monohydric alcohol having a total carbon number of 3 or less and a dihydric alcohol having a total carbon number of 3 or less being less than 10% by mass with respect to the mass of the emulsion composition, and
the pH of the emulsion composition being 6.5 or more.

[2] The emulsion composition according to [1], in which the content of the compound having a diaminopyrimidine skeleton is from 0.2% by mass to 5.0% by mass with respect to the mass of the emulsion composition.

[3] The emulsion composition according to [1] or [2], in which an average particle diameter of emulsified particles contained in the emulsion composition is 500 nm or less.

[4] The emulsion composition according to any one of [1] to [3], in which the sum total of the content of the monohydric alcohol having a total carbon number of 3 or less and the content of the dihydric alcohol having a total carbon number of 3 or less is less than 5% by mass with respect to the mass of the emulsion composition.

[5] The emulsion composition according to any one of [1] to [4], further including a polyhydric alcohol having a total carbon number of 4 or more.

[6] The emulsion composition according to any one of [1] to [5], in which the fatty acid having a total carbon number of 14 or more includes a fatty acid having 18 carbon atoms.

[7] The emulsion composition according to any one of [1] to [6], in which the fatty acid having a total carbon number of 14 or more includes at least one selected from the group consisting of isostearic acid and oleic acid.

[8] The emulsion composition according to any one of [1] to [7], in which the content of the fatty acid component is from 0.01% by mass to 20.0% by mass with respect to the mass of the emulsion composition.

[9] The emulsion composition according to any one of [1] to [8], further including an emulsifier having an HLB value of 10 or more.

[10] The emulsion composition according to any one of [1] to [9], in which the compound having a diaminopyrimidine skeleton is minoxidil.

[11] The emulsion composition according to [9] or [10], in which the emulsifier having an HLB value of 10 or more is at least one selected from the group consisting of a sucrose fatty acid ester, polysorbate, and polyoxyethylene hydrogenated castor oil.

[12] The emulsion composition according to any one of [9] to [11], in which the content of the emulsifier having an HLB value of 10 or more is from 0.1% by mass to 5.0% by mass with respect to the mass of the emulsion composition.

[13] A topical preparation for skin in which the emulsion composition according to any one of [1] to [12] is used.

Advantageous Effects of Invention

According to the invention, an emulsion composition containing a diaminopyrimidine derivative, and having favorable emulsion stability and favorable stability of the diaminopyrimidine derivative can be provided.

DESCRIPTION OF EMBODIMENTS

The emulsion composition according to the invention is an emulsion composition that includes: a compound having a diaminopyrimidine skeleton; at least one fatty acid component selected from the group consisting of a fatty acid having a total carbon number of 14 or more and a salt thereof; and an aqueous medium in an amount of 50% by mass or more with respect to the mass of the emulsion composition, the total amount of monohydric alcohol having a total carbon number of 3 or less and dihydric alcohol having a total carbon number of 3 or less in the emulsion composition being less than 10% by mass with respect to the mass of the emulsion composition, and the emulsion composition having a pH of 6.5 or more.

Hereinafter, the emulsion composition according to the invention is referred to as the "diaminopyrimidine derivative-containing emulsion composition".

According to the invention, the emulsion composition is configured to include a compound having a diaminopyrimidine skeleton (hereinafter referred to as a "diaminopyrimidine derivative"), to have a content of monohydric or dihydric alcohol having a total carbon number of 3 or less of less than 10% by mass, to include at least one fatty acid component selected from the group consisting of a fatty acid having a total carbon number of 14 or more and a salt thereof, and to have a pH of 6.5 or more, whereby the emulsion stability of the diaminopyrimidine derivative-containing emulsion composition and the stability of the diaminopyrimidine derivative are made favorable. As a result, it is made possible to prepare a pharmaceutical preparation containing minoxidil in a high concentration without substantially containing any monohydric or dihydric alcohol having a total carbon number of 3 or less, which would cause strong skin irritation.

Specifically, in a case in which a monohydric alcohol having a total carbon number of 3 or less, such as ethanol, or a dihydric alcohol having a total carbon number of 3 or less is used as a solubilizer, the diaminopyrimidine derivative is stable even at a pH on the acidic side, and generally used in the acidic region in consideration of prevention of coloring of the preparation, the solubility of the preparation, and the like (see Japanese Patent No. 4796260, in which a pH of from 5.7 to 6.3 is preferred). In contrast, we have found that, in the emulsion composition in which the content of monohydric alcohol having a total carbon number of 3 or less or of dihydric alcohol having a total carbon number of 3 or less is small, the diaminopyrimidine derivative decomposes with a lapse of time at a pH on the acidic side. Further, an emulsion composition having a pH on the acidic side has a decreased stability, and, for example, aggregation of the emulsified particles contained in the emulsion composition occurs. However, we have found that, even in an emulsion composition including a diaminopyrimidine derivative, adding at least one fatty acid component selected from the group consisting of a fatty acid having a total carbon number of 14 or more and a salt thereof, and further adjusting the pH to 6.5 or more makes it possible to suppress the decomposition of the diaminopyrimidine derivative due to acid, and to maintain favorable stability of the emulsion composition itself as well as favorable stability of the diaminopyrimidine derivative, owing to the fatty acid serving as an anionic surfactant to stabilize the emulsion. The invention is based on the findings.

Any numerical range indicated using "to" in the invention refers to a range including the numerical values noted before and after the "to" as the minimum value and the maximum value, respectively.

In the invention, in a case in which there are plural substances corresponding to a particular component in the emulsion composition, the amount of the component in the emulsion composition means the total amount of the multiple substances present in the emulsion composition, unless specified otherwise.

In the present specification, the term "step" includes not only an independent step, but also a step that cannot be clearly distinguished from another step as long as the intended purpose of the step of interest is achieved.

In the present specification, the "aqueous phase" means a phase in which an aqueous medium serves as a solvent, and the "oil phase" is used as a term contrasted with the "aqueous phase", regardless of the kind of the solvent therein.

Hereinafter, the invention will be described.

<Diaminopyrimidine Derivative>

The diaminopyrimidine derivative is not particularly limited as long as it is a compound having a diaminopyrimidine skeleton, and examples thereof include a diaminopyrimidine oxide compound. Examples of the diaminopyrimidine oxide compound include a 2-aminopyrimidine-4-3-oxide compound; a 2,4-diaminopyrimidine-3-oxide compound; a 2,4-diamino-6-alkoxypyrimidine-3-oxide compound; a 2,4-diaminopyrimidine-3-oxide compound substituted at the 6-position; a 2,4-diamino-6-alkoxypyrimidine-3-oxide compound, or a 2,4-diamino-6-thioalkylpyrimidine-3-oxide compound; a 2-alkyl-4-amino(or 2,4-dialkyl or 2,4-diamino) pyrimidine-3-oxide compound; a 6-haloalkoxypyrimidine-3-oxide compound; a 2,4,6-triaminopyrimidine-3-oxide compound; a 2,4-diamino-6-piperidinopyrimidine-3-oxide compound; and a 2,4-diamino-6-pyrrolidinopyrimidine-3-oxide compound. Among them, 2,4-diamino-6-piperidinopyrimidine-3-oxide (minoxidil) and 2,4-diamino-6-pyrrolidinopyrimidine-3-oxide are preferred for their hair growing activity, and minoxidil is particularly preferred.

The content of diaminopyrimidine derivative in the diaminopyrimidine derivative-containing emulsion composition is not particularly limited, and is preferably from 0.2% by mass to 5.0% by mass, more preferably from 0.2% by mass to 4.0% by mass, still more preferably from 0.2% by mass to 3.0% by mass, and particularly preferably from 0.2% by mass to 1.0% by mass, with respect to the mass of the emulsion composition. In a case in which the content is 0.2% by mass or more, there is a tendency that drug efficacy of the diaminopyrimidine derivative is easily exerted, and in a case in which the content is 5.0% by mass or less, there is a tendency that the drug efficacy is easily controllable.

<Fatty Acid Component>

In the diaminopyrimidine derivative-containing emulsion composition, a fatty acid component is contained. The fatty acid component is at least one selected from the group consisting of a fatty acid having a total carbon number of 14 or more and a salt thereof. In a case in which a fatty acid or a salt thereof is not contained, and in a case in which the total carbon atoms of the fatty acid or salt thereof is fewer than 14, the diaminopyrimidine derivative-containing emulsion composition dissolves in water, and an emulsion cannot be prepared. From the viewpoints of availability from natural products and ease in application to the human body, the total carbon atoms of the fatty acid component is preferably from 14 to 22, and more preferably from 18 to 22.

The fatty acid having a total carbon number of 14 or more may be a fatty acid having a linear or branched chain, and may be a saturated or unsaturated fatty acid. Further, the fatty acid having a total carbon number of 14 or more may have a substituent. The fatty acid having a total carbon number of 14 or more, including a salt thereof, may be used singly or in combination of two or more thereof. In a case in which two or more thereof are used in combination, the combination may be a combination of fatty acids, or a combination of fatty acid salts, or a combination of a fatty acid and a fatty acid salt.

Examples of the fatty acid having a total carbon number of 14 or more include myristic acid, palmitic acid, stearic acid, behenic acid, linoleic acid, linolenic acid, oleic acid, isostearic acid, arachidic acid, and behenic acid. Among them, as the fatty acid having a total carbon number of 14 or more, a fatty acid having a total carbon number of 18 is preferred from the viewpoints of suppression of the decomposition of the diaminopyrimidine derivative and ease in application to the human body; at least one selected from the group consisting of isostearic acid and oleic acid is more preferred from the viewpoint of the stability of the emulsion composition; isostearic acid is still more preferred from the viewpoints of a lower tendency to be oxidized and a lower tendency to color the emulsion composition; and an mixture of isomers of isostearic acid is particularly preferred from the viewpoint that the fatty acid is liquid at room temperature and does not solidify during storage at low temperatures over time when contained in an emulsion liquid. The mixture of isomers of isostearic acid is, for example, isostearic acid EX (trade name) manufactured by KOKYU ALCOHOL KOGYO CO., LTD.

Examples of a salt structure for forming the salt of a fatty acid having a total carbon number of 14 or more include a salt of an alkali metal such as sodium or potassium, a salt of a basic amino acid such as L-arginine, L-histidine, or L-lysine, and a salt of an alkanolamine such as triethanolamine. The kind of salt is appropriately selected depending on, for example, the kind of fatty acid to be used. From the viewpoint of the solubility and the dispersibility, an alkali metal salt such as a sodium salt is preferred. Among them, from the viewpoint of ease in application to the human body, the salt is preferably a salt of a fatty acid having a total carbon number of 18 or more, and more preferably an alkali metal salt of at least one fatty acid selected from the group consisting of isostearic acid and oleic acid.

The content of the fatty acid component in the diaminopyrimidine derivative-containing emulsion composition (the total content of the fatty acid component; for example, in a case in which a fatty acid having a total carbon number of 14 or more and a salt of a fatty acid having a total carbon number of 14 or more are combined and contained in the diaminopyrimidine derivative-containing emulsion composition, the sum total of the contents thereof) is preferably from 0.01% by mass to 20.0% by mass, more preferably from 1.0% by mass to 20.0% by mass, still more preferably from 1.0% by mass to 10.0% by mass, and particularly preferably from 3.0% by mass to 6.0% by mass, with respect to the mass of the emulsion composition from the viewpoint of suppressing the crystal precipitation of the diaminopyrimidine derivative.

<Aqueous Medium>

Media that may be contained in the diaminopyrimidine derivative-containing emulsion composition are not particularly limited, and examples thereof include water, and a mixed medium of water and a medium miscible therewith. The water, or the mixed medium of water and a medium miscible therewith, may include a freely selected component such as a pH adjusting agent. The aqueous medium may be an aqueous solution of such a freely selected component, and may be a buffer solution having buffering capacity. Examples of the freely selected component include an organic acid, an organic base, an inorganic acid, and an inorganic base, and a salt thereof. The content of aqueous medium in the diaminopyrimidine derivative-containing emulsion composition is 50% by mass or more, and more preferably 70% by mass or more.

With respect to organic acids, organic bases, inorganic acids, inorganic bases, and salts thereof that may be contained in the aqueous medium, specifically, aqueous solutions that include any of the following may be used: organic acids, such as citric acid, ascorbic acid, gluconic acid, tartaric acid, succinic acid, acetic acid, phthalic acid, trifluoroacetic acid, morpholino ethanesulfonic acid, and 2-(4-(2-hydroxyethyl)-1-piperazinyl) ethanesulfonic acid, and salts thereof; organic bases, such as tris(hydroxymethyl) aminomethane, and ammonia, and salts thereof; inorganic acids, such as hydrochloric acid, perchloric acid, carbonic acid, and phosphoric acid, and salts thereof; inorganic bases, such as sodium phosphate, potassium phosphate, calcium hydroxide, sodium hydroxide, potassium hydroxide, and magnesium hydroxide, and salts thereof; and inorganic hydrogen salts such as sodium hydrogen phosphate and sodium hydrogen carbonate. The aqueous solution is not limited to those described above.

<Monohydric Alcohol Having a Total Carbon Number of 3 or Less and Dihydric Alcohol Having a Total Carbon Number of 3 or Less>

In the diaminopyrimidine derivative-containing emulsion composition, the total amount (that is, the total content) of monohydric alcohol having a total carbon number of 3 or less and dihydric alcohol having a total carbon number of 3 or less (hereinafter referred to as "monohydric alcohol and dihydric alcohol with a total carbon number of 3 or less") is less than 10% by mass with respect to the total mass of the emulsion composition.

When the content of monohydric alcohol and dihydric alcohol with a total carbon number of 3 or less in the diaminopyrimidine derivative-containing emulsion composition is 10% by mass or more, there is a possibility that topical administration of the diaminopyrimidine derivative-containing emulsion composition to the skin or the like may cause irritation, the stability of the emulsion composition over time deteriorates, the decomposition of the diaminopyrimidine derivative over time occurs, and, therefore, the stability of the emulsion composition over time and the stability of the diaminopyrimidine derivative over time are not obtained.

From the viewpoint of skin irritation, the content of monohydric alcohol and dihydric alcohol with a total carbon number of 3 or less is, in terms of the total amount thereof, preferably less than 5% by mass, more preferably less than 1% by mass, and particularly preferably 0% by mass; that is, it is particularly preferable that the diaminopyrimidine derivative-containing emulsion composition does not contain any monohydric or dihydric alcohols having a total carbon number of 3 or less.

Examples of monohydric alcohols having a total carbon number of 3 or less include ethanol, methanol, propanol, and isopropanol.

Examples of dihydric alcohols having a total carbon number of 3 or less include propylene glycol and ethylene glycol.

<Auxiliary Emulsifier>

The diaminopyrimidine derivative-containing emulsion composition may further contain an emulsifier, as a component that may additionally be contained. Inclusion of an emulsifier in the diaminopyrimidine derivative-containing emulsion composition enables further reduction of the average particle diameter of the emulsified particles contained in the diaminopyrimidine derivative-containing emulsion composition, and improvement of the emulsion stability.

The scope of the emulsifier that may additionally be contained in the diaminopyrimidine derivative-containing emulsion composition (hereinafter referred to as an "auxiliary emulsifier") does not include fatty acids having a total carbon number of 14 or more and salts thereof. From the viewpoint of emulsification power, the auxiliary emulsifier is preferably an auxiliary emulsifier having an HLB value of 10 or more, and more preferably an auxiliary emulsifier having an HLB value of 12 or more. However, an auxiliary emulsifier having an HLB value of from 5 to less than 10 may be used from the viewpoint of a foam suppression effect. The HLB value of an auxiliary emulsifier is a balance of hydrophilicity and hydrophobicity used in the field of surfactants, and generally used calculation formulae, for example, the Kawakami equation, may be used. The Kawakami equation is presented below.

$$HLB = 7 + 11.7 \log(M_W/M_O)$$

In the equation, $M_W$ is the molecular weight of hydrophilic group(s), and $M_O$ is the molecular weight of hydrophobic group(s).

Further, the numerical values of HLB described in catalogs or the like may be used.

Examples of the auxiliary emulsifier having an HLB value of 10 or more include anionic surfactants, cationic surfactants, and nonionic surfactants. Among auxiliary emulsifiers, a nonionic surfactants are preferred due to, for example, their low irritating property and small influence on the environment. Examples of nonionic surfactants include a sucrose fatty acid ester, a polyglycerol fatty acid ester, an organic acid monoglyceride, a propylene glycol fatty acid ester, a polyglycerin condensed ricinoleic acid ester, a sorbitan fatty acid ester, a polyoxyethylene sorbitan fatty acid ester, polyoxyethylene hydrogenated castor oil, polyoxyl stearate, and polyoxyethylene behenyl ether.

As the sucrose fatty acid ester, a sucrose fatty acid ester in which the number of carbon atoms of the fatty acid forming the sucrose fatty acid ester is from 12 to 20 is preferable, and a sucrose fatty acid ester in which the number of carbon atoms of the fatty acid forming the sucrose fatty acid ester is from 14 to 18 is more preferable, from the viewpoint of the stability of the emulsified particles contained in the emulsion composition.

Preferable examples of the sucrose fatty acid ester include a sucrose trioleate ester, a sucrose tristearate ester, a sucrose tripalmitate ester, a sucrose trimyristate ester, a sucrose trilaurate ester, a sucrose dioleate ester, a sucrose distearate ester, a sucrose dipalmitate ester, a sucrose dimyristate ester, a sucrose dilaurate ester, a sucrose monooleate ester, a sucrose monostearate ester, a sucrose monopalmitate ester, a sucrose monomyristate ester, and a sucrose monolaurate ester. Among them, a sucrose monooleate ester, a sucrose monostearate ester, a sucrose monopalmitate ester, a sucrose monomyristate ester, and a sucrose monolaurate ester are more preferred.

In the invention, these sucrose fatty acid esters may be used singly or in combination of two or more thereof.

As the sorbitan fatty acid ester, a sorbitan fatty acid ester in which the number of carbon atoms of the fatty acid is 8 or more is preferred, and a sorbitan fatty acid ester in which the number of carbon atoms of the fatty acid is 12 or more is more preferred. Preferable examples of the sorbitan fatty acid ester include sorbitan monocaprylate, sorbitan monolaurate, sorbitan monostearate, sorbitan sesquistearate, sorbitan tristearate, sorbitan isostearate, sorbitan sesquiisostearate, sorbitan oleate, sorbitan sesquioleate, and sorbitan trioleate. These sorbitan fatty acid esters may be used singly, or in combination of two or more thereof.

As the polyoxyethylene sorbitan fatty acid ester, a polyoxyethylene sorbitan fatty acid ester in which the number of carbon atoms of the fatty acid is 8 or more is preferred, and a polyoxyethylene sorbitan fatty acid ester in which the number of carbon atoms of the fatty acid is 12 or more is more preferred. Further, the length (average molar number of addition) of ethylene oxide of the polyoxyethylene is preferably from 2 to 100, more preferably from 4 to 50, and particularly preferably from 10 to 25. Preferable examples of the polyoxyethylene sorbitan fatty acid ester include polyoxyethylene sorbitan monocaprylate, polyoxyethylene sorbitan monolaurate, polyoxyethylene sorbitan monostearate, polyoxyethylene sorbitan sesquistearate, polyoxyethylene sorbitan tristearate, polyoxyethylene sorbitan isostearate, polyoxyethylene sorbitan sesquiisostearate, polyoxyethylene sorbitan monooleate, polyoxyethylene sorbitan sesquioleate, and polyoxyethylene sorbitan trioleate.

With respect to the polyoxyethylene hydrogenated castor oil, the length (average molar number of addition) of ethylene oxide of the polyoxyethylene is preferably from 2 to 100, and more preferably from 10 to 60.

From the viewpoints of decreasing the particle diameter of the emulsion and improving the emulsion stability, the auxiliary emulsifier more preferably includes a sucrose fatty acid ester, a polyoxyethylene sorbitan fatty acid ester (also referred to as a "polysorbate"), polyoxyethylene hydrogenated castor oil, or the like, and particularly preferably includes a polysorbate.

The content of auxiliary emulsifier is preferably from 0.1% by mass to 5.0% by mass, and more preferably from 0.5% by mass to 5.0% by mass, with respect to the total mass of the diaminopyrimidine derivative-containing emulsion composition. Setting the content of auxiliary emulsifier to be 0.1% by mass or more provides a tendency that more favorable emulsion stability is obtained. Setting the content of auxiliary emulsifier to be 5.0% by mass or less provides a tendency that coloring by the auxiliary emulsifier can be suppressed.

From the viewpoints of decreasing the particle diameter of the emulsion and enhancing the emulsion stability, the ratio of the content of auxiliary emulsifier to the content of fatty acid component is preferably from 0.1 to 2.0, more preferably from 0.2 to 1.7, and still more preferably from 0.2 to 1.0.

<Other Components>

The diaminopyrimidine derivative-containing emulsion composition may include, in addition to the above-described components, other components that can generally be added into emulsion compositions. Other components may be mixed as an aqueous phase composition or an oil phase composition of the diaminopyrimidine derivative-containing emulsion composition.

The diaminopyrimidine derivative-containing emulsion composition preferably includes a polyhydric alcohol having a total carbon number of 4 or more, from the viewpoints of the transparency of the emulsion composition, the improvement of the temporal stability of the emulsion, the improvement of the stability of the diaminopyrimidine derivative, and the anti-septic properties, and from the viewpoint of the moisture retaining property when the diaminopyrimidine derivative-containing emulsion composition is applied to the skin or the like.

Examples of the polyhydric alcohol having a total carbon number of 4 or more include polyglycerol, 3-methyl-1,3-butanediol, 1,3-butylene glycol, isoprene glycol, polyethylene glycol, 1,2-pentanediol, 1,2-hexanediol, dipropylene glycol, neopentyl glycol, sorbitol, xylitol, sodium hyaluronate, sodium chondroitin sulfate, pullulan, pectin, gum arabic, carrageenan, an alginic acid propylene glycol ester, carboxymethyl cellulose, hydroxypropyl cellulose, hydroxyethyl cellulose, hydroxypropyl methyl cellulose, and methyl cellulose. These polyhydric alcohols having a total carbon number of 4 or more may be used singly, or in the form of a mixture of two or more thereof.

The content of polyhydric alcohol having a total carbon number of 4 or more is preferably from 0.1% by mass to 20.0% by mass, and more preferably from 1.0% by mass to 15.0% by mass, with respect to the total amount of the composition from the viewpoint of the transparency of the emulsion composition, the improvement of the temporal stability of the emulsion, the improvement of the stability of the diaminopyrimidine derivative, and the anti-septic properties, and from the viewpoint of the moisture retaining property when the diaminopyrimidine derivative-containing emulsion composition is applied to the skin or the like.

The diaminopyrimidine derivative-containing emulsion composition may include a monohydric alcohol having a total carbon number of 4 or more. Examples of the monohydric alcohol having a total carbon number of 4 or more include butanol, lauryl alcohol, oleyl alcohol, isostearyl alcohol, 2-decyltetradecanol, cholesterol, and phytosterol. These monohydric alcohols having a total carbon number of 4 or more may be used singly, or in the form of a mixture of two or more thereof. The content of monohydric alcohol having a total carbon number of 4 or more is preferably 10.0% by mass or less, and more preferably 5.0% by mass or less, with respect to the total amount of the emulsion composition.

The diaminopyrimidine derivative-containing emulsion composition may include a pH adjusting agent, as appropriate. The pH adjusting agent may be used either before or after the preparation of the final emulsion composition. From the viewpoints of decreasing a change in pH and enabling the pH to be adjusted under milder conditions, the pH adjusting agent is preferably used before the preparation of the final emulsion composition. In this case, the pH adjusting agent may be added to either the aqueous phase composition or the oil phase composition before the preparation of the final emulsion composition.

The diaminopyrimidine derivative-containing emulsion composition may include a physiologically active component other than the diaminopyrimidine derivative. The physiologically active component other than the diaminopyrimidine derivative is not particularly limited as long as it is a component that is absorbed from the skin and exhibit an activity; the physiologically active component other than the diaminopyrimidine derivative can, for example, be selected from a cosmetic ingredient, a quasi drug ingredient, or a pharmaceutical ingredient. Examples of physiologically active components that may be included in the diaminopyrimidine derivative-containing emulsion composition include a moisturizer, a whitening agent, a hair restorer, a hair tonic, a hair grower, a blood circulation promotion agent, an anti-white hair agent, an anti-aging agent, an anti-oxidant, a collagen synthesis promoter, an anti-wrinkle agent, an anti-pimple agent, vitamins, an ultraviolet absorbent, a flavor, a pigment, a deodorant, a cool-feeling agent, a warm feeling agent, a melanin formation inhibitor, a melanocyte activator, an anti-biotic, an anti-cancer agent, an anti-inflammatory agent, an anti-allergic agent, a hormonal drug, an anti-thrombus agent, an immunosuppressive agent, a dermatosis therapeutic agent, an anti-fungal agent, a nucleic acid medicine, an anesthetic, an anti-pyretic, an analgesic, an anti-pruritic agent, an anti-edemic agent, a sedative hypnotic, an anti-anxiety agent, a stimulant, a drug for psycho neurosis, a muscle relaxant, an anti-depressant, a combination cold remedy, an autonomic nervous system drug, an anti-spasmodic agent, a diaphoretic, an anti-perspirant, a cardiac stimulant, an agent for treating cardiac arrhythmia, an anti-arrhythmic agent, a vasoconstrictor, a vasodilator, an anti-arrhythmic agent, an anti-hypertensive agent, an agent for treating diabetes, a drug for hyperlipemia, a respiratory stimulant, an anti-tussive, vitamins, a drug for parasitic skin disease, a homeostatic drug, a polypeptide, a hormone, a parakeratosis inhibitor, a vaccine, and a skin softener. The above-described physiologically active components may be used singly, or in combination of two or more thereof.

The diaminopyrimidine derivative-containing emulsion composition may include a pharmaceutically acceptable oily component (oil agent) that is used as a base material of an oil phase, and that can form an oil phase. Examples of such an oil agent in the invention include: medium-chain fatty acid triglycerides; long-chain fatty acid triglycerides such as vegetable oils (that is, natural triglycerides), chemically synthesized triglycerides, and animal oils; mineral oils; synthetic oils; essential oils; and ester oils; and mixtures thereof.

A medium-chain fatty acid triglyceride means a fat or an oil in which the average carbon number of the fatty acid chains forming the triglyceride contained in the medium-chain fatty acid triglyceride is 12 or less. Examples of fatty acids for forming fatty acid chains include a fatty acid having from 6 to 12 carbon atoms. These constituent fatty acids in a medium-chain fatty acid triglyceride may be saturated or unsaturated. Preferably, the medium-chain fatty acid triglyceride is mainly formed of a triglyceride of a saturated fatty acid having from 6 to 12 carbon atoms. The medium-chain fatty acid triglyceride may be derived from natural vegetable oil or a triglyceride of a synthetic fatty acid. These may be used singly, or in combination of two or more thereof.

A long-chain fatty acid triglyceride means a fat or an oil in which the average carbon number of the fatty acid chains forming the triglyceride contained in the long-chain fatty acid triglyceride is larger than 12. The fatty acid forming each fatty acid chain may be a saturated fatty acid or an unsaturated fatty acid. Examples of the long-chain fatty acid triglyceride include a vegetable oil, which corresponds to a natural triglyceride, and a chemically synthesized triglyceride.

Specific examples of the vegetable oil include soybean oil, cottonseed oil, rapeseed oil, sesame oil, safflower oil, corn oil, peanut oil, olive oil, coconut oil, *perilla* oil, and castor oil. Among them, soybean oil is preferred.

Examples of the chemically synthesized triglyceride include 2-linoleoyl-1,3-dioctanoyl glycerol.

The diaminopyrimidine derivative-containing emulsion composition may further include various additives. As an additive, for example, one or more selected from a moisturizer, a softening agent, a transdermal absorption promoting agent, an analgesic agent, an anti-septic, an anti-oxidant, a coloring agent, a thickener, or a flavor may be used. As these various additives, conventionally known additives may be used without particular limitations.

<pH>

The pH of the diaminopyrimidine derivative-containing emulsion composition is 6.5 or more. When the pH of the diaminopyrimidine derivative-containing emulsion composition is less than 6.5, there is a tendency that the diaminopyrimidine derivative decomposes, and the temporal stability of the emulsion is also impaired. The pH of the diaminopyrimidine derivative-containing emulsion composition is preferably from 6.5 to less than 10.0, more preferably from 7.0 to less than 10.0, and particularly preferably from 7.0 to 8.3. When the pH is less than 10.0, the diaminopyrimidine derivative-containing emulsion composition is easily applicable to proteins constituting hairs.

From the viewpoint of the transparency and the emulsion stability of the emulsion composition, the average particle diameter of emulsified particles (oil droplets) contained in the diaminopyrimidine derivative-containing emulsion composition is preferably 500 nm or less, and more preferably 200 nm or less. The lower limit value of the average particle diameter of the emulsified particles contained in the diaminopyrimidine derivative-containing emulsion composition is not particularly limited, and may be set to be, for example, 0.8 nm or more.

The average particle diameter of emulsified particles in the invention means the volume average particle diameter of emulsified particles present in the diaminopyrimidine derivative-containing emulsion composition. The average particle diameter of emulsified particles contained in the diaminopyrimidine derivative-containing emulsion composition is measured using a dynamic light scattering method in view of the accuracy and the simplicity of measurement.

Examples of commercially available measuring apparatuses using dynamic light scattering include a concentrated system particle size analyzer FPAR-1000 (manufactured by Otsuka Electronics Co., Ltd.), NANOTRAC UPA (manufactured by NIKKISO CO., LTD.), and NANOSIZER (manufactured by Malvern Instruments Ltd). As the average particle diameter of emulsified particles in the invention, a value obtained by a measurement at 23° C. using a concentrated system particle size analyzer FPAR-1000 (manufactured by Otsuka Electronics Co., Ltd.) is adopted. Specifically, the diaminopyrimidine derivative-containing emulsion composition as a measurement sample is diluted 10 fold with Milli-Q water and a measurement is performed, and the average particle diameter is obtained as a median diameter (d=50).

Further, the average particle diameter of emulsified particles can be adjusted based on the components of the emulsion composition as well as other factors such as stirring conditions (shearing force, temperature, pressure) in the production method or the ratio of the oil phase to the aqueous phase.

<Production Method of Diaminopyrimidine Derivative-Containing Emulsion Composition>

The diaminopyrimidine derivative-containing emulsion composition includes an aqueous medium in an amount of 50% by mass or more, and, therefore, the diaminopyrimidine derivative-containing emulsion composition is in the form of an oil-in-water emulsion composition. Therefore, the diaminopyrimidine derivative-containing emulsion composition can be obtained using a conventionally known method for obtaining an oil-in-water emulsion composition. Specifically, the diaminopyrimidine derivative-containing emulsion composition can be prepared, for example, as follows. An oil phase component (which means a component capable of forming an oil phase), such as a fatty acid component, and a diaminopyrimidine derivative are mixed and stirred to obtain an oil phase composition. An aqueous phase component (which means a component capable of forming an aqueous phase) is mixed into an aqueous medium or the like and stirred to obtain an aqueous phase composition. The obtained oil phase composition and aqueous phase composition are mixed and emulsified, thereby obtaining the diaminopyrimidine derivative-containing emulsion composition.

The mixing ratio (mass) between the oil phase composition and the aqueous phase composition is not particularly limited. The ratio of the oil phase composition/the aqueous phase composition (% by mass) is preferably from 0.1/99.9 to 50/50, more preferably from 0.5/99.5 to 30/70, and still more preferably from 1/99 to 20/80.

Setting the ratio of the oil phase composition/the aqueous phase composition to be not lower than 0.1/99.9 enables active components to be used in sufficient additions amounts, and thus provides a tendency that the diaminopyrimidine derivative-containing emulsion composition does not have practical problems. Therefore, such a ratio is preferred. Setting the ratio of the oil phase composition/the aqueous phase composition to be not higher than 50/50 prevents the emulsifier concentration from becoming low, and provides a tendency that the stability of the emulsion composition is easily maintained.

The mixing and emulsifying the oil phase composition and the aqueous phase composition preferably includes mixing the oil phase composition and the aqueous phase composition to obtain a coarse emulsion composition, and then subjecting the coarse emulsion composition to micronization using a fine emulsification means.

As a means for mixing the oil phase composition and the aqueous phase composition to obtain a coarse emulsion composition, any of commercially available mixing means may be used. For example, mixing and stirring the aqueous medium using a magnetic stirrer, a mixer for domestic use, a paddle mixer, or an impeller mixer enables preparation of a homogeneous coarse emulsion liquid. Further, the mixing of the oil phase composition and the aqueous phase composition is preferably carried out using a stirring means having a strong shear force, such as a homomixer, a disper mixer, or an ultra mixer, is more preferable.

Further, it is also preferable to utilize ultrasonic waves for the purpose of enhancing the effect of coarse emulsification, in addition to these stirring means. As a means for applying ultrasonic waves, an ultrasonic homogenizer is preferably used. Examples of the ultrasonic homogenizer include Ultrasonic homogenizer US-160, Ultrasonic homogenizer US-600, Ultrasonic homogenizer US-1200T, Ultrasonic homogenizer RUS-1200T, and Ultrasonic homogenizer MUS-1200T (which are manufactured by NIHONSEIKI KAISHA LTD.), and Ultrasonic Processor UIP2000, Ultrasonic Processor UIP-4000, Ultrasonic Processor UIP-8000, and Ultrasonic Processor UIP-16000 (which are manufactured by Hielscher).

These high power ultrasonic irradiation apparatuses may be used at a frequency of 25 kHz or less, and preferably from 15 kHz to 20 kHz.

Further, as other mixing means, a static mixer, a microchannel, a micromixer, and the like, which does not have stirring parts connected to the outside and which requires only a low energy, are also usable.

With respect to the temperature in the coarse emulsification treatment, the treatment can be performed at any temperature of from 20° C. to 90° C., and preferably at a temperature of from 20° C. to 80° C.

Next, the coarse emulsion composition obtained is preferably micronized using a fine emulsification means.

As the means for micronization, a high-pressure homogenizer is preferably used. High-pressure homogenizers are able to apply a large shear force as compared to stirring systems, and therefore are capable of micronization; various apparatuses thereof are commercially available.

Examples of high-pressure homogenizers include chamber-type high-pressure homogenizers such as MICROFLUIDIZER (manufactured by Microfluidics Corporation), NANOMIZER (manufactured by YOSHIDA KIKAI CO., LTD.), and STAR BURST (manufactured by SUGINO MACHINE LIMITED), and homogenizing valve-type high-pressure homogenizers such as Gaulin-type homogenizers (manufactured by APV), Rannie-type homogenizers (manufactured by Rannie), high-pressure homogenizers (manufactured by Niro Soavi), homogenizers (manufactured by Sanwa Machine Co., Inc.,), high-pressure homogenizers (manufactured by IZUMI FOOD MACHINERY CO., LTD.), and ultra high-pressure homogenizers (manufactured by IKA).

As the conditions of emulsification using a high-pressure homogenizer, the pressure is preferably 100 MPa or more, and more preferably 150 MPa or more, from the viewpoint of dispersibility (micronization). The limit value at the high pressure side is preferably 300 MPa or less in commercially available apparatuses from the viewpoint of pressure resistance; however, from the viewpoint of temperature elevation, it is estimated that the limit value may be set to be 400 MPa or less in the case of dispersion in an aqueous medium.

In a case in which micronization is performed using a fine emulsification means, the number of times high pressure treatment is performed may be 1; however, in order to increase the homogeneity of the entire liquid, it is preferable to perform high pressure treatment twice or more times, and it is more preferable to perform high pressure treatment 2 to 20 times.

From the viewpoint that the coloring due to an auxiliary emulsifier is less noticeable, the temperature before the high pressure dispersion treatment is preferably set to be from 25° C. to 70° C., and more preferably from 25° C. to 50° C. It is preferred to perform rapid cooling using a cooling means immediately after the high pressure dispersion treatment, thereby decreasing the temperature to a predetermined temperature. As the cooling apparatus, any commercially available heat exchanger may be used.

The diaminopyrimidine derivative-containing emulsion composition obtained by the method described above is an emulsion composition which has emulsion stability over time and stability of the diaminopyrimidine derivative over time, and in which a diaminopyrimidine derivative is dissolved in a sufficient amount even though the total amount of monohydric alcohol and dihydric alcohol with a total carbon number of 3 or less is less than 10% by mass.

In the invention, the emulsion stability over time of the diaminopyrimidine derivative-containing emulsion composition is evaluated through visual observation of the outer appearance. Specifically, evaluation is performed based on, for example, whether or not the separation between the oil phase and the aqueous phase is observed, whether or not neck ring (a phenomenon that emulsified particles coming up to the liquid surface adhere, in a ring shape, to the wall surface of an upper part of the vessel) is observed, or whether or not the generation of aggregates is observed by visual observation of the diaminopyrimidine derivative-containing emulsion composition.

In the invention, the stability over time of the diaminopyrimidine derivative is evaluated by performing quantification by a high performance liquid chromatograph of the residual ratio of the diaminopyrimidine derivative in the diaminopyrimidine derivative-containing emulsion composition, using samples before and after storage.

<Applications>

The diaminopyrimidine derivative-containing emulsion composition can be used as a topical preparation for skin for transdermal administration to the human body, and is particularly preferably used as a topical preparation for skin for the scalp.

EXAMPLES

Hereinafter, the invention will be described in detail with reference to Examples. However, the invention is not limited thereto.

Example 1

<Preparation of Emulsion Liquid (C-1)>

Into a 110-mL vial in which a stirring bar was placed, 2.5 g of isostearic acid (mixture) (ISOSTEARIC ACID EX (trade name, the same shall apply hereinafter) manufactured by KOKYU ALCOHOL KOGYO CO., LTD.) and 5.0 g of 1,3-butylene glycol (manufactured by Wako Pure Chemical Industries, Ltd.) were added, and stirred at room temperature for 10 minutes. 0.6 g of minoxidil (manufactured by SOLMAG) was added thereto, and then a pre-prepared mixed liquid of 2.0 g of a sodium hydroxide solution (manufactured by Wako Pure Chemical Industries, Ltd., 1 mol/L) and 39.9 g of Milli-Q water was further added thereto. The resultant was stirred at room temperature for 3.5 hours. The mixed liquid obtained was left to stand at room temperature for 12 hours, and then subjected to a high-pressure emulsification treatment using a high-pressure homogenizer, as a result of which an intended emulsion liquid (C-1) containing emulsified particles having a particle diameter of 223 nm (minoxidil concentration: 1.2% by mass, pH: 8.0) was obtained.

Example 2

<Preparation of Emulsion Liquid (C-2)>

Into a 110-mL vial in which a stirring bar was placed, 2.5 g of isostearic acid (mixture) (ISOSTEARIC ACID EX manufactured by KOKYU ALCOHOL KOGYO CO., LTD.) and 5.0 g of 1,3-butylene glycol (manufactured by Wako Pure Chemical Industries, Ltd.) were added, and stirred at room temperature for 10 minutes. 0.6 g of minoxidil (manufactured by SOLMAG) was added thereto, and then a pre-prepared mixed liquid of 5.0 g of a sodium hydroxide solution (manufactured by Wako Pure Chemical Industries, Ltd., 1 mol/L) and 35.2 g of Milli-Q water, and 1.7 g of a sucrose fatty acid ester (DK ESTER F-90 (trade name, the same shall apply hereinafter) manufactured by Dai-ichi Kogyo Seiyaku Co., Ltd., which is a sucrose stearic acid ester (monosubstituted product: 45%, disubstituted and trisubstituted products: 55%, HLB value: 9.5)) were further added thereto. The resultant was stirred at room temperature for 3.5 hours. The mixed liquid obtained was left to stand at room temperature for 12 hours, and then subjected to a high-pressure emulsification treatment using a high-pressure homogenizer under the same conditions as those in Example 1, as a result of which an intended emulsion liquid (C-2) containing emulsified particles having a particle diameter of 40 nm (minoxidil concentration: 1.2% by mass, pH: 8.3) was obtained.

Example 3

<Preparation of Emulsion Liquid (C-3)>

An intended emulsion liquid (C-3) containing emulsified particles having a particle diameter of 54 nm (minoxidil concentration: 1.2% by mass, pH: 8.3) was obtained in the same manner as that in Example 2, except that the 1.7 g of the sucrose fatty acid ester (DK ESTER F-90) described in Example 2 was replaced by 0.5 g of a sucrose fatty acid ester (DK ESTER SS (trade name, the same shall apply hereinafter) manufactured by Dai-ichi Kogyo Seiyaku Co., Ltd., which is a sucrose stearic acid ester (monosubstituted product: 100%, HLB value: 19)).

Example 4

<Preparation of Emulsion Liquid (C-4)>

Into a 200-mL stainless steel cup in which a stirring bar was placed, 2.5 g of soybean oil (manufactured by Wako Pure Chemical Industries, Ltd.), 2.5 g of isostearic acid (2-heptyl undecanoic acid manufactured by Wako Pure Chemical Industries, Ltd.), and 5.0 g of 1,3-butylene glycol (manufactured by Wako Pure Chemical Industries, Ltd.) were sequentially added, and stirred at room temperature for 10 minutes. 0.6 g of minoxidil (manufactured by SOLMAG) was added thereto, and then a pre-prepared mixed liquid of 0.5 g of a sodium hydroxide solution (manufactured by Wako Pure Chemical Industries, Ltd., 1 mol/L) and 37.9 g of Milli-Q water, and 1.0 g of a sucrose fatty acid ester (DK ESTER F-160 (trade name, the same shall apply hereinafter) manufactured by Dai-ichi Kogyo Seiyaku Co., Ltd., which is a sucrose stearic acid ester (monosubstituted product: 70%, disubstituted and trisubstituted products: 30%, HLB value: 15)) were further added thereto. The resultant was irradiated with ultrasonic waves (ultrasonic homogenizer US-600T, manufactured by NIHONSEIKI KAISHA LTD.) at 0° C. for 10 minutes. The mixed liquid obtained was further subjected to a high-pressure emulsification treatment using a high-pressure homogenizer under the same conditions as those in Example 1, as a result of which an intended emulsion liquid (C-4) containing emulsified particles having a particle diameter of 109 nm (minoxidil concentration: 1.2% by mass, pH: 7.4) was obtained.

Example 5

<Preparation of Emulsion Liquid (C-5)>

An intended emulsion (C-5) containing emulsified particles having a particle diameter of 107 nm (minoxidil concentration: 1.2% by mass, pH: 7.0) was obtained in the same manner as that in Example 4, except that the sucrose fatty acid ester (DK ESTER F-160) described in Example 4 was replaced by a sucrose fatty acid ester (DK ESTER SS manufactured by Dai-ichi Kogyo Seiyaku Co., Ltd., HLB value: 19).

Example 6

<Preparation of Emulsion Liquid (C-6)>

Into a 110-mL vial in which a stirring bar was placed, 2.5 g of isostearic acid (mixture) (ISOSTEARIC ACID EX manufactured by KOKYU ALCOHOL KOGYO CO., LTD.) and 5.0 g of 1,3-butylene glycol (manufactured by Wako Pure Chemical Industries, Ltd.) were added, and stirred at room temperature for 10 minutes. 0.6 g of minoxidil (manufactured by SOLMAG) was added thereto, and then a pre-prepared mixed liquid of 5.0 g of a sodium hydroxide solution (manufactured by Wako Pure Chemical Industries, Ltd., 1 mol/L) and 34.4 g of Milli-Q water, and 0.5 g of polyoxyethylene hydrogenated castor oil (NIKKOL HCO-60 (for medicament) (product name) manufactured by Nikko chemicals Co., Ltd., HLB value: 14) were further added thereto. The resultant was stirred at room temperature for 3.5 hours. The mixed liquid obtained was left to stand at room temperature for 12 hours, and then subjected to a high-pressure emulsification treatment using a high-pressure homogenizer, as a result of which an intended emulsion (C-6) containing emulsified particles having a particle diameter of 171 nm (minoxidil concentration: 1.2% by mass, pH: 8.0) was obtained.

Example 7

<Preparation of Emulsion Liquid (C-7)>

An intended emulsion liquid (C-7) containing emulsified particles having a particle diameter of 40 nm (minoxidil concentration: 1.2% by mass, pH: 7.9) was obtained in the same manner as that in Example 6, except that the polyoxyethylene hydrogenated castor oil described in Example 6 was replaced by POLYSORBATE 80 (manufactured by Wako Pure Chemical Industries, Ltd., a product equivalent to Tween 80, HLB value: 15).

Example 8

<Preparation of Emulsion Liquid (C-8)>

Into a 200-mL stainless steel cup in which a stirring bar was placed, 10.0 g of soybean oil (manufactured by Wako Pure Chemical Industries, Ltd.), 5.0 g of sodium oleate (manufactured by Wako Pure Chemical Industries, Ltd.), and 10.0 g of 1,3-butylene glycol (manufactured by Wako Pure Chemical Industries, Ltd.), were sequentially added, and stirred at room temperature for 10 minutes. 1.2 g of minoxidil (manufactured by SOLMAG) was added thereto, and then 73.8 g of Milli-Q water was further added thereto. The resultant was irradiated with ultrasonic waves (ultrasonic homogenizer US-600T, manufactured by NIHONSEIKI KAISHA LTD.) at 0° C. for 10 minutes. The mixed liquid obtained was further subjected to a high-pressure emulsification treatment using a high-pressure homogenizer, as a result of which an intended emulsion liquid (C-8) containing emulsified particles having a particle diameter of 234 nm (minoxidil concentration: 1.2% by mass, pH: 9.5) was obtained.

Comparative Example 1

Into a 110-mL vial in which a stirring bar was placed, 5.0 g of 1,3-butylene glycol (manufactured by Wako Pure Chemical Industries, Ltd.) and 0.6 g of minoxidil (manufactured by SOLMAG) were added. Then, a pre-prepared mixed liquid of 0.1 g of a sodium hydroxide solution (manufactured by Wako Pure Chemical Industries, Ltd., 0.1 mol/L) and 44.3 g of Milli-Q water was further added thereto, and stirred at room temperature for 3.5 hours. The mixed liquid obtained was left to stand at room temperature for 12 hours, and then was subjected to a high-pressure treatment using a high-pressure homogenizer, as a result of which an intended aqueous solution (R-1) (minoxidil concentration: 1.2% by mass, pH: 7.0) was obtained.

Comparative Example 2

<Preparation of Emulsion Liquid (R-2)>

An intended emulsion liquid (R-2) containing emulsified particles having a particle diameter of 515 nm (minoxidil concentration: 1.2% by mass, pH: 6.4) was obtained in the same manner as that in Example 8, except that the sodium oleate described in Example 8 was replaced by isostearic acid (mixture) (ISOSTEARIC ACID EX manufactured by KOKYU ALCOHOL KOGYO CO., LTD.), and that the pH was adjusted to 6.4.

Comparative Example 3

<Preparation of Emulsion Liquid (R-3)>

In a 110-mL vial, 0.5 g of minoxidil (manufactured by SOLMAG), 1.5 g of isostearic acid (mixture) (ISOSTEARIC ACID EX (trade name) manufactured by KOKYU ALCOHOL KOGYO CO., LTD.), 2.0 g of polyoxyethylene hydrogenated castor oil (NIKKOL HCO-40 (for medicament) (product name) manufactured by Nikko chemicals Co., Ltd., HLB value: 12.5), 5.0 g of 1,3-butylene glycol (manufactured by Wako Pure Chemical Industries, Ltd.), and 7.5 g of Milli-Q water were stirred, and heated to 80° C. 21.0 g of the Milli-Q water heated to 80° C. was added thereto and stirred, and cooled to room temperature. Into the mixed liquid obtained, 5.0 g of ethanol and 7.5 g of Milli-Q water were further added and stirred, as a result of which an intended emulsion liquid (R-3) containing emulsified particles having a particle diameter of 10 nm (minoxidil concentration: 1.0% by mass, pH: 5.8, containing 10% by mass of ethanol) was obtained.

Comparative Example 4

<Preparation of Emulsion Liquid (R-4)>

In a 110-mL vial, 0.5 g of minoxidil (manufactured by SOLMAG), 1.5 g of isostearic acid (mixture) (ISOSTEARIC ACID EX (trade name) manufactured by KOKYU ALCOHOL KOGYO CO., LTD.), 2.0 g of polyoxyethylene hydrogenated castor oil (NIKKOL HCO-40 (for medicament) (product name) manufactured by Nikko chemicals Co., Ltd., HLB value: 12.5), 5.0 g of 1,3-butylene glycol (manufactured by Wako Pure Chemical Industries, Ltd.), and 7.5 g of Milli-Q water were stirred and heated to 80° C. 20.9 g of Milli-Q water heated to 80° C. and 0.1 g of phosphoric acid (manufactured by Wako Pure Chemical Industries, Ltd., with a grade for food additives) were added thereto and stirred, and cooled to room temperature. Into the mixed liquid obtained, 5.0 g of ethanol and 7.5 g of Milli-Q water were further added and stirred, as a result of which an intended emulsion liquid (R-4) containing emulsified particles having a particle diameter of 127 nm (minoxidil concentration: 1.0% by mass, pH: 4.2, containing 10% by mass of ethanol) was obtained.

Evaluation

<Evaluation of Emulsion Liquids>

The emulsion liquids and the aqueous solutions of (C-1) to (C-8) and (R-1) to (R-4), which were obtained in the above, were subjected to the evaluation of outer appearance and the evaluations of particle diameter measurement, emulsion stability, and stability of the compound, in the manner described below. The results of the evaluations are indicated in Table 1. In Table 1, "−" in the compositions means non-addition (0% by mass) or means that there is no corresponding item, and "−" in the evaluation results means that the evaluation was impossible.

(1) Evaluation of Outer Appearance

The emulsion liquids and aqueous solutions were stored at room temperature for one week from immediately after the liquid preparation, and visually observed. Based on the state of separation between the oil phase and the aqueous phase in each emulsion, evaluation was made in accordance with the following.

A: The oil phase and the water phase do not separate.

B: The oil phase and the water phase separate, but uniformly mix within one minute when the vial is shaken.

C: The oil phase and the water phase separate, and do not uniformly mix within one minute even when the vial is shaken.

(2) Particle Diameter Measurement 0.2 mL of each emulsion liquid was mixed with 1.8 mL of Milli-Q water, to obtain a measurement sample. Particle diameter measurement was performed on the measurement sample under the condition of 23° C. using a dynamic light scattering particle size distribution analyzer FPAR-1000 (manufactured by Otsuka Electronics Co., Ltd.). The value of the average particle diameter was indicated in terms of median diameter.

(3) Emulsion Stability 3.0 mL of each emulsion liquid or aqueous solution was added into a 5.0 mL vial, and the vial was stored in a thermostat bath at 60° C. for two weeks. The emulsion liquid after the storage was returned to room temperature, and then the outer appearance was visually observed. Based on the presence or absence of a deposited matter on the wall face of each vial (hereinafter referred to as a "vial deposited matter") and the presence or absence of a precipitate, evaluation was made in accordance with the following. A vial wall face contacting the liquid surface portion of the emulsion liquid or aqueous solution was used as the vial wall for determination of the presence or absence of a vial deposited matter.

S: A vial deposited matter is not observed, and a precipitate is not observed either.

A: There is a vial deposited matter, but uniform liquid is restored within one minute by shaking the vial. Further, a precipitate was not observed.

B: There is a vial deposited matter, and uniform liquid is not restored even by shaking the vial for one minute or longer. Further, a precipitate was not observed.

C: A vial deposited matter was not observed, but a precipitate was observed.

(4) Stability of Compound 3.0 mL of each emulsion liquid or aqueous solution was added into a 5.0 mL vial, and the vial was stored in a thermostat bath at 60° C. for two weeks. About 10 mg of the emulsion liquid or aqueous solution after the storage was weighed into a 10-mL measuring flask, and the liquid in the flask was diluted to 10 mL, to obtain a post-storage sample liquid. A pre-storage sample liquid was obtained for each emulsion liquid before storage by performing sample preparation in the same manner as that in the above. Quantification of minoxidil was performed for the post-storage sample liquid and the pre-storage sample liquid using a high performance liquid chromatograph (column: CAPCELLPAK C-18 manufactured by Shiseido Co., Ltd., detector: UV detector, detection wavelength: 280 nm). As the standard sample, a minoxidil drug substance (manufactured by SOL-MAG) was used. The storage stability was evaluated based on the amount of minoxidil in the post-storage sample liquid to the amount of minoxidil in the pre-storage sample liquid in terms of the proportion (% residual ratio) obtained by multiplying the area ratio by 100. Evaluation based on the area ratio is in accordance with the following.

A: The area ratio is 97% or higher
B: The area ratio is lower than 97%

TABLE 1

| Emulsion Liquid or Aqueous Solution | Minoxidil (% by mass) | Fatty Acid/Fatty Acid Salt Kind | Content (% by mass) | Auxiliary Emulsifier Kind | HLB value | Content (% by mass) | Oil agent (% by mass) | Ethanol (% by mass) | pH | Outer Appearance | Particle Diameter (nm) | Emulsion Stability | Stability of Compound |
|---|---|---|---|---|---|---|---|---|---|---|---|---|---|
| (C-1) | 1.2 | Isostearic Acid | 5.0 | None | — | — | — | 0.0 | 8.0 | A | 223 | A | A |
| (C-2) | 1.2 | Isostearic acid | 5.0 | Sucrose fatty acid ester (DK ESTER F-90) | 9.5 | 3.5 | — | 0.0 | 8.3 | A | 40 | A | A |
| (C-3) | 1.2 | Isostearic acid | 5.0 | Sucrose fatty acid ester (DK ESTER SS) | 19 | 3.5 | — | 0.0 | 7.9 | A | 54 | S | A |
| (C-4) | 1.2 | Isostearic acid | 5.0 | Sucrose fatty acid ester (DK ESTER F-160) | 15 | 2.0 | 5.0 | 0.0 | 7.4 | A | 109 | S | A |
| (C-5) | 1.2 | Isostearic acid | 5.0 | Sucrose fatty acid ester (DK ESTER SS) | 19 | 2.0 | 5.0 | 0.0 | 7.0 | A | 107 | S | A |
| (C-6) | 1.2 | Isostearic acid | 5.0 | Polyoxyethylene hydrogenated castor oil (Nikkol HCO-60) | 14 | 1.0 | — | 0.0 | 8.0 | A | 171 | S | A |
| (C-7) | 1.2 | Isostearic acid | 5.0 | Polysorbate 80 | 15 | 1.0 | — | 0.0 | 7.9 | A | 40 | S | A |
| (C-8) | 1.2 | Sodium oleate | 5.0 | None | — | 0.0 | 10.0 | 0.0 | 9.5 | A | 234 | A | A |
| (R-1) | 1.2 | None | — | None | — | 0.0 | — | 0.0 | 7.0 | A | — | C | A |
| (R-2) | 1.2 | Isostearic acid | 5.0 | None | — | 0.0 | 10.0 | 0.0 | 6.4 | B | 515 | B | B |
| (R-3) | 1 | Isostearic acid | 3.0 | Polyoxyethylene hydrogenated castor oil (Nikkol HCO-40) | 12.5 | 4.0 | — | 10.0 | 5.8 | A | 10 | S | B |
| (R-4) | 1 | Isostearic acid | 3.0 | Polyoxyethylene hydrogenated castor oil (Nikkol HCO-40) | 12.5 | 4.0 | 0.0 | 10.0 | 4.2 | A | 127 | S | B |

As indicated in Table 1, it was found, from the results of the evaluation of emulsion stability, that minoxidil precipitated with a lapse of time in aqueous solution (R-1), which does not include a fatty acid.

Further, in the evaluation of the outer appearance and the emulsion stability, emulsion liquid (R-2) having a pH of 6.4 was a white cloudy liquid in which the oil phase and the aqueous phase separated, and the separated oil phase floated as oil. In the evaluation of the stability of the compound, emulsion liquid (R-2) produced a result in which the residual ratio at 60° C. over two weeks was a low value that is lower than 97%. Therefore, it was found that, in emulsion liquid (R-2), the emulsion stability and the stability of the compound were both inferior.

Further, emulsion liquids (R-3) and (R-4), which include ethanol in an amount of 10% by mass or more, both had a pH of less than 6.5, and the residual ratio of minoxidil was lower than 97%. Therefore, presumably, the decomposition by acid progresses at a low pH of less than 6.5.

In contrast, all of emulsion liquids (C-1) to (C-8), which correspond to working examples of the invention, exhibited favorable results in terms of all of the outer appearance evaluation, the emulsion stability evaluation, and the evaluation of the stability of the compound.

More specifically, in emulsion liquid (C-1), which includes isostearic acid and has a pH of 8.0, and in emulsion liquid (C-8), which includes sodium oleate and has a pH of 9.5, a white cloudy liquid free of separation between oil and water was obtained in the outer appearance evaluation and the emulsion stability evaluation. Further, in the evaluation of the stability of the compound, a result with a residual ratio of 97% or higher was obtained.

Furthermore, each of emulsion liquids (C-1) to (C-8) includes neither a monohydric alcohol having a total carbon number of 3 or less nor a dihydric alcohol having a total carbon number of 3 or less; therefore, it is expected that the emulsion liquids are not irritative to the skin.

In addition, emulsion liquids (C-3), (C-6), and (C-7), each of which includes an auxiliary emulsifier having an HLB value of 10 or more and has a pH of from 7.9 to 8.3, exhibited an average particle diameter that is still smaller than those of emulsion liquids (C-1) and (C-8) in the particle diameter measurement, and, also in terms of outer appearance, clouding was less noticeable in emulsion liquids (C-3), (C-6), and (C-7). Further, with respect to the emulsion stability of emulsion liquids (C-3), (C-6), and (C-7), a deposited matter was not observed on the vial wall even after the storage at 60° C. It is conceivable that these results are produced because the hydrophilicity of emulsified matter was enhanced by the addition of an emulsifier having a high HLB value, and the emulsified matter becomes to have a reduced tendency to attach to the hydrophobic vial wall. This indicates that the emulsion stability is improved by the inclusion of an emulsifier having a high HLB value. Further, a stability of the compound of 97% or higher was also maintained, as in emulsion (C-1).

In addition, similar to the case of emulsion liquid (C-3), results in which both of the emulsion stability and the stability of the compound were achieved were also obtained for emulsion liquid (C-4) having a pH of 7.4 and emulsion liquid (C-5) having a pH of 7.0, each of which includes an auxiliary emulsifier having an HLB value of 10 or more.

As described above, according to the invention, a diaminopyrimidine derivative-containing emulsion composition having favorable emulsion stability and favorable stability of a diaminopyrimidine derivative can be provided.

The disclosure of Japanese Patent Application No. 2013-017644, filed Jan. 31, 2013, is incorporated herein by reference in its entirety.

All publications, patent applications, and technical standards mentioned in this specification are incorporated herein by reference to the same extent as if such individual publications, patent applications, and technical standards are specifically and individually indicated to be incorporated by reference.

The invention claimed is:

1. An emulsion composition comprising:
a compound having a diaminopyrimidine skeleton;
at least one fatty acid component selected from the group consisting of a fatty acid having a total carbon number of 14 to 22 and a salt thereof; and
an aqueous medium in an amount of 50% by mass or more with respect to a mass of the emulsion composition,
a total amount of a monohydric alcohol having a total carbon number of 3 or less and a dihydric alcohol having a total carbon number of 3 or less being less than 1% by mass with respect to the mass of the emulsion composition, wherein
a pH of the emulsion composition is in a range of 6.5 or more and less than 10.0,
an average particle diameter of emulsified particles contained in the emulsion composition is 500 nm or less, and
the emulsion composition is obtained by micronization using a fine emulsification process.

2. The emulsion composition according to claim 1, wherein a content of the compound having a diaminopyrimidine skeleton is from 0.2% by mass to 5.0% by mass with respect to the mass of the emulsion composition.

3. The emulsion composition according to claim 1, further comprising a polyhydric alcohol having a total carbon number of 4 or more.

4. The emulsion composition according to claim 1, wherein the fatty acid having a total carbon number of 14 to 22 includes a fatty acid having 18 carbon atoms.

5. The emulsion composition according to claim 1, wherein the fatty acid having a total carbon number of 14 to 22 includes at least one selected from the group consisting of isostearic acid and oleic acid.

6. The emulsion composition according to claim 1, wherein a content of the fatty acid component is from 0.01% by mass to 20.0% by mass with respect to the mass of the emulsion composition.

7. The emulsion composition according to claim 1, further comprising an emulsifier having an HLB value of 10 or more.

8. The emulsion composition according to claim 1, wherein the compound having a diaminopyrimidine skeleton is minoxidil.

9. The emulsion composition according to claim 7, wherein the emulsifier having an HLB value of 10 or more is at least one selected from the group consisting of a sucrose fatty acid ester, polysorbate, and polyoxyethylene hydrogenated castor oil.

10. The emulsion composition according to claim 7, wherein a content of the emulsifier having an HLB value of 10 or more is from 0.1% by mass to 5.0% by mass with respect to the mass of the emulsion composition.

11. A topical preparation for skin in which the emulsion composition according to claim 1 is used.

* * * * *